United States Patent [19]

Nilsson

[11] Patent Number: 5,532,147
[45] Date of Patent: Jul. 2, 1996

[54] ENZYMATIC METHOD FOR SYNTHESIS OF CARBOHYDRATES

[76] Inventor: Kurt Nilsson, Andjaktsv. 6, Lund, Sweden, 222 53

[21] Appl. No.: 190,162

[22] PCT Filed: Jun. 8, 1992

[86] PCT No.: PCT/SE92/00541

§ 371 Date: Apr. 6, 1994

§ 102(e) Date: Apr. 6, 1994

[87] PCT Pub. No.: WO93/03168

PCT Pub. Date: Feb. 18, 1993

[30] Foreign Application Priority Data

Aug. 6, 1991 [SE] Sweden ................... 9102292

[51] Int. Cl.$^6$ .................. C12P 19/12; C12P 19/64
[52] U.S. Cl. ................ 435/100; 435/73; 435/74; 435/101; 435/200; 536/123.13; 536/123.1
[58] Field of Search ................ 435/73, 74, 100, 435/101, 200; 536/123.13, 123.1

[56] References Cited

U.S. PATENT DOCUMENTS 4,918,009  4/1990  Nilsson .................... 435/73
5,246,080  9/1993  Nilsson .................... 435/101

FOREIGN PATENT DOCUMENTS 0404964   1/1991   European Pat. Off. .
451849   11/1987   Sweden .
87/05936 10/1987   WIPO .
91/02806  3/1991   WIPO .

*Primary Examiner*—John W. Rollins
*Assistant Examiner*—Francisco C. Prats
*Attorney, Agent, or Firm*—Beveridge, DeGrandi, Weilacher & Young

[57] ABSTRACT

A synthetic method in which is included at least one process, which is characterized by that a glycosidase (EC 3.2) is used to catalyse a reaction between a partially protected galactose derivative, or a partially protected glucose derivative, and a glycosyl doner, which is an oligosaccharide or a monosaccharide glycoside, is described. The process is suitable for synthesis of carbohydrate derivatives or for synthesis of partially protected carbohydrate intermediates which are suitable for further synthesis e.g. of blood group determinants A and B, or other carbohydrates.

34 Claims, No Drawings

ENZYMATIC METHOD FOR SYNTHESIS OF CARBOHYDRATES

The present invention relates to a procedure for synthesis of derivatives of galactose containing carbohydrates and of glucose containing carbohydrates which are suitable for further synthesis of, for example, biological receptor structures, such as blood group determinants, or of other derivatives which can be used directly in medical/diagnostical applications.

Carbohydrates have a central function in living organisms, in the metabolism, as an energy source, for protection against the environment, as biological markers, as receptor substances and as antigenic determinants. The oligosaccharide part of glycoproteins and glycolipids are important in vivo (Biology of Carbohydrates, vol. 2, Ginsburg et al., Wiley, New York, 1984; The Glycoconjugates, vol. I-V, Academic Press, New York; S. Hakomori, Ann. Rev. Biochem., vol. 50, pp. 733–64; Feizi, Nature, pp. 314, 1985; S. Hakomori, Chemistry and Physics of Lipids, vol. 42, pp. 209–33). Among other things it was found that

- the carbohydrate structures are important for the stability, activity, localisation, immunogenicity and degradation of glycoproteins;
- carbohydrates are antigenic determinants (for example blood group antigens);
- carbohydrates function as receptors when bound to cell surfaces for pathogens, proteins, hormones, toxins and during cell-cell interactions;
- carbohydrates are important for oncogenesis, since specific oligosaccharides have been found to be cancer-associated antigenic determinants;
- frequently, only a smaller sequence (di- or trisaccharide) of the carbohydrate part of the glycoconjugate is required for full biological activity (e.g. receptor activity).

Oligosaccharide derivatives which contain one or more modified/derivatised monosaccharide units, for example deoxy-, phospho-, sulphate-, derivatised amino- or thio groups, are of high interest for pharmaceutical or diagnostic applications of carbohydrates, to modify the metabolism of the substance and/or to increase the biological effect of the natural substance.

Carbohydrate derivatives are also used in general as synthetic intermediates to achieve selective organic-chemical synthesis of carbohydrates (see e.g. Binkley: Modern Carbohydrate Chemistry, Marcel Dekker, New York, 1988, with references). Selective chemical syntheses of carbohydrates require advanced protection group chemistry with many synthetic steps, inter alia because the syntheses of selectively modified carbohydrate intermediates are complicated. Efficient techniques for preparation of such carbohydrate intermediates are thus desired.

The present invention describes a process which makes possible a drastically simplified synthesis of derivatised/modified di-, tri-, and higher oligosaccharides. Carbohydrate derivatives which required several reaction steps to synthesise with previous methods, can, with the method according to the present invention, now be obtained with only one reaction step and with absolute stereospecificity, which also is different from chemical methods, where more or less poisonous reagents, e.g. Ag-triflate or mercury cyanide, have been used and where the desired $\alpha$- or $\beta$-isomer was obtained together with the undesired stereoisomer.

The synthetic method according to the invention includes at least one process characterised by that a glycosidase (EC 3.2) is used to catalyse an equilibrium or a transglycosylation reaction between an acceptor substance, which consists of either a galactose derivative or a glucose derivative, and a glycosyl donor, which is a monosaccharide, oligosaccharide or a glycoside, and that the product is used for continued synthesis and/or is isolated from the product mixture. In this way one obtains, according to the invention, stereospecific synthesis of di-, tri-, or higher oligosaccharide derivatives, which can be used directly, or after further synthesis, for a number of various applications, e.g. for pharmaceutical/medical/diagnostical studies, for applications in therapy, diagnostics, as additives in cosmetics or in food, for modification of separation material, affinity chromatography, modification of amino acids, peptides, proteins, fatty acids, lipids, enzymes, recombinant proteins.

In the synthesis according to the invention, the capacity of glycosidases to form stereospecific glycosidic linkages between a glycosyl donor (DOR in the scheme below, where D symbolises the transferred carbohydrate part) and a glycosyl acceptor (HOA), summarised in the scheme below:

$$DOR + HOA \rightleftharpoons DOA + HOR \qquad (1)$$

The reaction according to the invention can be carried out according to two principles, either with equilibrium controlled synthesis (R=H), or with transglycosylation reaction (R=F, or an organic group; kinetically controlled reaction). These type of reactions are well known to the expert and their carrying out, as well as the choice of glycosyl donor and glycosidase, do not restrict the scope of the invention.

Examples of acceptor substances which can be used with the method according to the invention is D-galactal, D-glucal, and D-galactal or D-glucal, which has been modified with one or more organic or inorganic group in one or more of the positions C-3, C-4, C-5 or C-6, and D-galactopyranose- or D-glucopyranose, which has been modified with one or several organic or inorganic groups in one or more of the of the positions C-2, C-3, C-4 or C-6, or a glycoside of such derivatives. Similar derivatives of N-acetyl-glucopyranose and N-acetyl-galactopyranose can also be used in the method according to the invention.

In the figures below, structures are exemplified, which can be used as acceptor substances (HOA in scheme 1 above) to form the oligosaccharide derivatives according to the invention. The structures symbolise derivatised/modified D-galactopyranose and D-glucopyranose, respectively ($R_1=R_2=R_3=R_4=R_6=$OH in D-galactopyranose and in D-glucopyranose; $R_2=$NHAc in N-acetyl-glucosamine and in N-acetylgalactosamine; Ac=acetyl group, Ph=phenyl group, Bz=bensoyl group, All=allyl group).

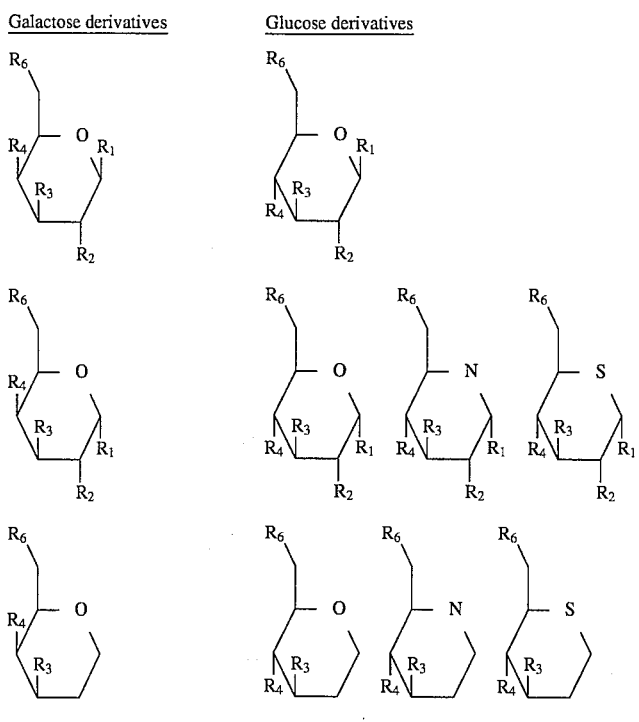

Where Ri (i=1–6) is hydroxyl (—OH), —F, or an inorganic or organic group and at least one and maximum three of $R_2$, $R_3$, $R_4$, or $R_6$ is not a hydroxyl group. -$R_1$ can for example be one of —OH, —F, —OMe, —OAll, —OPh, —OCH$_2$Ph, —OEtBr, —OEtSiMe$_3$, —O(CH$_2$)$_3$CH=CH$_2$, —SMe, —SEt, —SPh, carbohydrate, lipid- or amino acid- or peptide derivative or another group bound to the anomeric carbon. Any of —$R_2$, —$R_3$, —$R_4$, and/or —$R_6$, can for example be one of the above mentioned groups or one of for example —NHAc, NHC(O)CH$_2$Cl (N-chloromethoxyacetyl), NHC(O)CH$_2$OPh (N-phenoxyacetyl-), —NHBOC, —NHOH, —N$_3$, p-methoxybenzyl ether (—OCH$_2$Ph-OMe-p), trityl group (—OC(Ph)$_3$), trialkylsilyl ether group, pivaloyl-group, tetrahydropyranyl, (2-methoxyethoxy)methylisopropylidene ketal, cyclohexylidene ketal, benzylidene acetal, orthoester, —ONO3, tosylate-, mesylate-, sulphate-, phosphate-, carboxylate group, derivative of sulphate-, phosphate-, carboxylate, esters i.e. of the type —OC(O)R as acetyl-, butanoyl-, octanoyl-, bensoyl-, pivaloyl-, etc. The structures below, modified in a similar way, can also be used as acceptor substances in the method according to the invention.

The choice of the type of modification of the acceptor is decided by what is desired in the specific situation and the literature is rich in information on protection groups/modification of carbohydrates and carbohydrate synthesis in general (e.g. "Modern Carbohydrate Chemistry", Binkley, Marcel Dekker, 1988 with references and Paulsen, Chem. Soc. Rev. 13, p. 15–45). Below are a few examples of acceptor substance categories which can be used according to the invention but which in no way are meant to restrict the scope of the invention. Structures I–XI are galactose derivatives and XII–XVII are N-acetylglucosamine derivatives. Anhydrosugars symbolised with structures VII and VIII can also be used according to the invention.

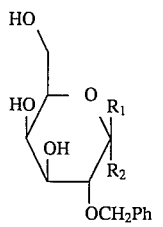 I

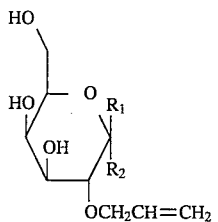 II

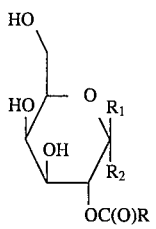 III

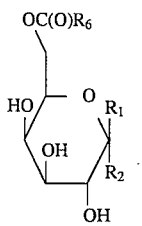 IV

-continued

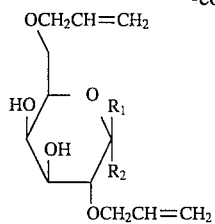

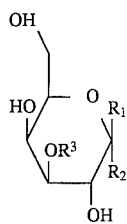

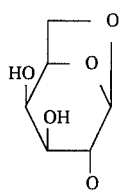

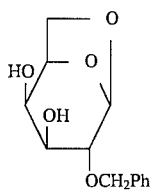

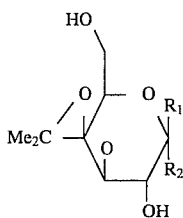

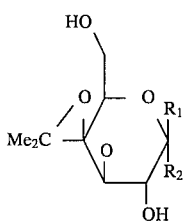

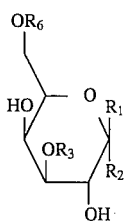

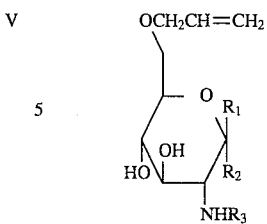 V

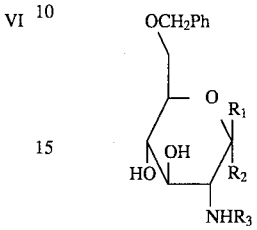 VI

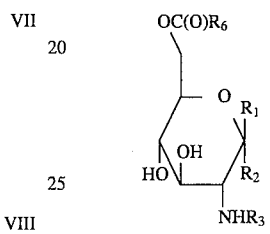 VII

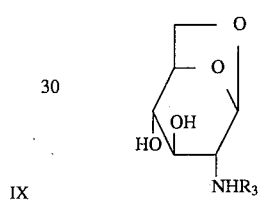 VIII

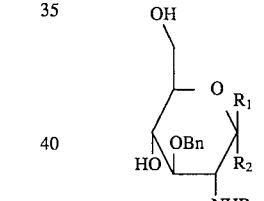 IX

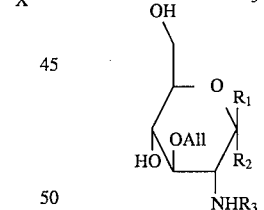 X

XI

-continued

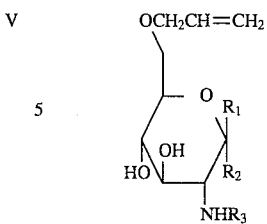 XII

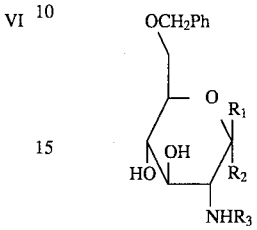 XIII

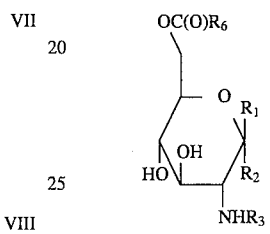 XIV

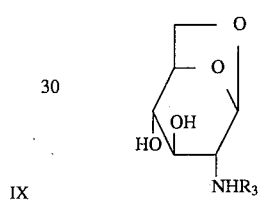 XV

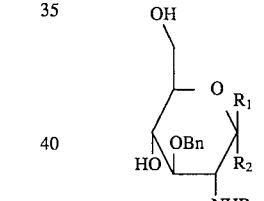 XVII

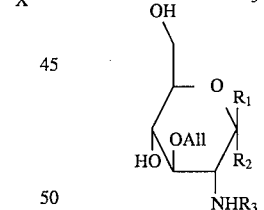 XVI $R_1$ or $R_2$ = H

In the structures I–XI above, $R_3$ is for example an alkyl, benzyl-, chlorobenzyl, bensoyl-group or another type of suitable protection group for the specific synthesis. $R_6$ can be an aromatic group such as Ph- or an alkyl group (e.g. propyl- or $(CH_3)_3$-group). In the structures XII–XVII, $R_3$ is for example an acetyl-, phenoxyacetyl-, methoxyacetyl- or an chlorometoxyacetyl group. $R_6$ can be an aromatic group, such as Ph- or an alkyl group (e.g. propyl- or $(CH_3)_3$-group).

If $R_2$ for example is H, then $R_1$ is one of the groups which has been mentioned for $R_1$ on page four above, and vice versa if $R_1$ instead is H.

As an example to illustrate the invention, but which in no way is meant to limit the scope of the invention, can be mentioned that if, for example, α-galactosidase is used as enzyme and an α-D-galactopyranose protected in position C-2 is used as acceptor substance, e.g. substance I above, and if $R_2$ is for example HO—, MeO—, PhCHO— or a $CH_2$=CH—$CH_2$O-group, and if, for example, raffinose, methyl α-D-galactopyranoside, or p-nitrophenyl α-D-galactopyranoside is used as glycosyl donor (transglycosylation reaction), an α-glycosidically linked digalactosyl derivative of the type

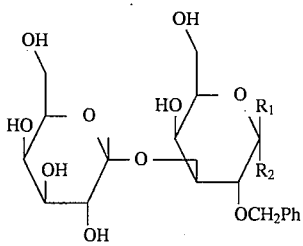

i.e a 2-0-derivative of Galα1-3Galα-R, is obtained. As another example, if I is used as acceptor and an α-galactosaminidase, e.g. from Chamelea gallina, and e.g. GalNAcα-OPh, or GalNAcα-OPhNO$_2$-p, is used as glycosyl donor, a 2-O-derivative of GalNAcα1-3Galα-R is obtained.

The products can be used for further synthesis, e.g. of higher oligosaccharides with chemical synthesis and the literature is extensive on how to use such partially protected carbohydrates (see references in Binkley and Paulsen mentioned above). As an example, the —OCH$_2$Ph group can be removed after protection of hydroxyl groups and substituted for by e.g. an α-bound L-fucopyranosyl group, and in this way blood group determinant A and B are synthesised from the 2-0-protected derivative of GalNAcα1-3Gal-R and Galα1-3Gal-R, respectively.

If a β-galactosidase is used instead of an α-galactosidase and if lactose,or for example p-nitrophenyl-β-D-galactopyranoside, is used as glycosyl donor, and if an N-acetyl-glucosamine derivative (see e.g. XII–XVII above) is used as acceptor, β-bound derivatives of Gal-GlcNAc-R is obtained. Examples of such partially protected Gal-GlcNAc-derivatives, which can be used e.g. for chemical synthesis of Lewis-x or Lewis-a trisaccharide structures (or which can be used for further chemical synthesis of disaccharide derivatives of these) are given below:

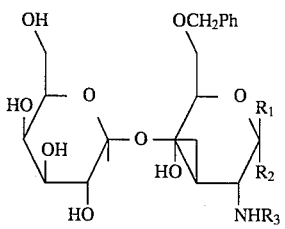

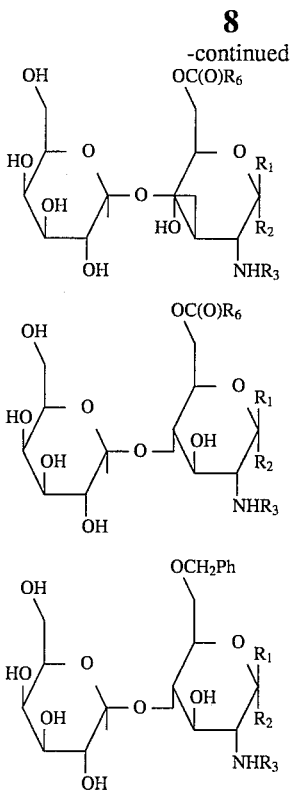

Moreover, if instead an α-fucosidase is used with, for example, nitrophenyl α-L-fucopyranoside as glycosyl donor, one can synthesise the corresponding derivatives of α-bound Fuc-Gal-R and of α-bound Fuc-GlcNAc-R with the method according to the invention. With N-acetyl-β-glucosaminidase or N-acetyl-β-galactosaminidase one can prepare derivatives of β-bound GlcNAc-Gal and GlcNAc-GlcNAc-R or GalNAc-Gal-R and GalNAc-GlcNAc, respectively, with β-glycosides of GlcNAc and GalNAc, respectively, as glycosyl donors. Similarly, α-sialidase can be used to catalyse synthesis of sialylated galactose-derivatives (derivatives of Neu5Acα-Gal) or of galactosamine-derivatives (derivatives of Neu5Acα-GalNAc) by employing e.g. nitrophenyl glycoside of N-acetylneuraminic acid and a partially protected galactose derivative or galactosamine derivative, respectively, as acceptor.

If an endoglycosidase is used, one can prepare longer oligosaccharide derivatives with the method according to the invention.

The reactions above can also be carried out as equilibrium reactions with monosaccharides as glycosyl donors.

Different derivatives of glucofuranose, such as 1,2-isopropylidene-α-D-glucofuranoside (structure 18 below), can also be used as acceptors with the method according to the invention.

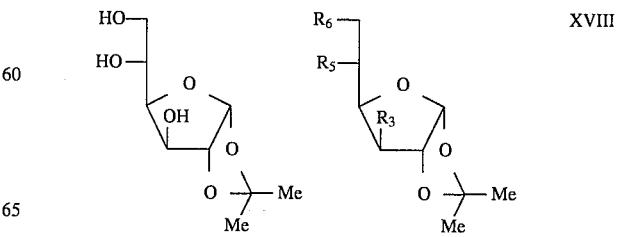

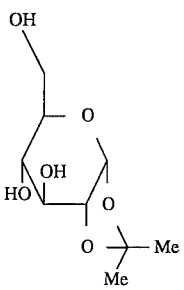

Different oligosaccharide derivatives of 1,2-isopropylidene-α-D-glucofuranoside, e.g. 3-derivatives of 1,2-0-isopropylidene-α-D-glucofuranose, such as 1,2-O-isopropylidene-3-O-3'-(N',N'-dimetylamino-n-propyl)-D-glucofuranose HCl (below called therafectin, a substance which is active in reumathoid arthritis, psoriasis, some types of cancer and asthma—Gordon, P., see Chemical Abstracts volume 95, abstract nr 54887 and Inflammation: Mech. Treat. Proc. Int. Meet., 4th 1980, 169–80, University Park Press, Baltimore), can thus be synthesised with the method according to the invention, by either using 18 as acceptor (the disaccharide product is modified in the 3-position after the enzymatic reaction) or the 3-modified derivative of 18. Not limiting examples of how this can be achieved with the method according to the invention is

- to react therafectin or analogs thereof with for example lactose or nitrophenyl β-galactoside using β-galactosidase (from e.g. *E. coli eller Aspergillus niger*) as catalysts in a suitable solvent. In this way one obtains therafektin modified with a β-glycosidically bound galactopyranosyl group. This substance can thereafter be used in pharmaceutical or cosmetic applications or be used for continued chemical or enzymatic synthesis. For example, further carbohydrate groups can be added to the product obtained in the first reaction by repeated glycosidase-catalysed synthesis with the same or another glycosidase, or by using for example sialyltransferase and CMP-Neu5Ac for synthesis of Neu5Acα2-3Galβ1-O-therafectin or of the corresponding 2-6-derivative. The galactosyl derivative can eventually be chemically modified before these latter reactions.
- In a similar manner, therafectin or analogs thereof can be reacted with for example GlcNAcβ-OR, GalNAcβ-OR, Manβ-OR, Galα-OR, Glcβ-OR (R=F, H, alkyl-, aryl- or a carbohydrate group) using glucosaminidase, galactosaminidase, mannosidase, galactosidase or glucosidase as catalyst.
- In a similar manner one can use an endoglycosidase as catalyst and an oligosaccharide or an oligosaccharide-derivative as glycosyl donor and with therafectin or an analog thereof as acceptor.

The reactions above can also be carried out as equilibrium controlled reactions with a simple monosaccharide as glycosyl donor.

The benzyl- or the allyl group (or other groups mentioned in connection with the figures above) in the products above, can easily be chemically changed by the expert to a wide range of other groups than L-fucose, and in this way selective synthesis of several different disaccharide derivatives (e.g. O-phosphate, O-sulphate, etc) or higher oligosaccharides can be selectively synthesised according to the invention.

Moreover, the products can be used for further enzymatic synthesis with glycosidases or glycosyltransferases. For example, α-sialyltransferase can be used to catalyse the formation of sialylated Gal-GlcNAc-derivatives and β-galactosyltransferase can be used to form oligosaccharide derivatives of the type Gal-GlcNAG-Gal-R, which then can eventually be sialylated and/or be used for further chemical synthesis, etc.

If a modified galactoside or glucoside is used as acceptor, the choice of aglycon is made with regard to the application of the product. Aglycons of special interest is amino acids (serine, threonine, hydroxyproline, hydroxylysine, asparagine, etc.), peptides, lipids and derivatives or analogs of substances within these three groups. Amino acid or peptide glycosides can be protected on their amino- and/or carboxyl functions with common groups used in peptide synthesis (FMOC, CBZ, BOC, etc.). Products obtained with modified alkyl glycosides (e.g. modified methyl-, octyl-, dodecyl glycosides) as acceptor substances, may be used as inhibitors in affinity chromatography or in agglutination tests, inhibition-based therapy or for drug-targeting, as structural units for further enzymatic synthesis. Nitrophenyl glycosides can be reduced to aminophenyl glycosides. Glycosides with a polymerisable aglycon, as for example 2-hydroxyethylmethacrylate, can be used. As an example of a N-glycosidically bonded aglycon, —NHCO(CH$_2$)SNH$_2$, may be mentioned. Other types of aglycons which can be used are those used e.g. in the synthesis of glycolipids/analogs for conversion to ceramides/analogs, e.g. aglycons of the type described by Magnusson et al. in J. Org. Chem., 1990. Thioglycosides (e.g. —SEt or —SPh) can be used with the method according to the invention to produce products which are suitable for further chemical synthesis. The choice of protection group/derivative, aglycon, position of derivatised hydroxyl groups, can be used to influence the yield and regioselectivity of the reactions with the method according to the invention. Thus, for example, the use of more hydrophobic aglycons (e.g. p-metoxy-benzyl-, benzyl-, compared with e.g. allyl-) can result in a higher yield at the same acceptor concentration.

The donor substrates which can be used in the method according to the invention are the same as those employed previously with glycosidases in synthesis via equilibrium or transglycosylation controlled reactions.

As examples of donor substances that can be used with the procedure according to the invention may be mentioned monosaccharides, monosaccharide glycosides and di- or oligosaccharides (or glycosides thereof) in which the carbohydrate part contains one or more of the monosaccharides D-galactose, D-mannose, N-acetyl-neuraminic acid, N-acetyl-D-galactosamine, N-acetyl-D-glucosamine and L-fucose. As examples of suitable glycosyl donors may be mentioned the nitrophenyl α- or β-glycosides of the monosaccharides above, lactose, dimannose and raffinose. Suitable donor substances for endoglycosidases are for example nitrophenyl glycosides of biologically active carbohydrate sequences (e.g. Galβ1-3-GlcNAcβ-OPhNO$_2$-p), biologically active oligosaccharides or structures of the type Glc(β1-3Glc)$_n$β1-3Glc (n>1).

The concentration of the glycosyl donor in the reaction mixture is selected with regard to the oligosaccharide which is to be synthesised and also with regard to the properties of the enzyme and therefore do not restrict the use of the invention. In general, addition of the donor in smaller portions may be advantageous in transglycosylation reactions in order to minimise the risk that the donor also acts as an acceptor. In equilibrium reactions a high initial concentration of donor is often preferrable.

The enzyme is selected primarily with regard to the oligosaccharide derivative which is to be synthesised. The enzyme may be used in situ or after partial or complete purification from their natural environment. The enzyme may be used in soluble form or immobilised to a solid support by e.g. adsorption, encapsulation, chelation, precipitation or covalent binding.

Examples of α- and β-glycosidases which may be used according to the invention are D-mannosidases, D-galactosidases, L-fucosidases, N-acetyl-D-galactosaminidases, hexosaminidases and other glycosidases of EC group 3.2 (Enzyme Nomenclature, Academic Press, 1984). Both endo- and exoglycosidases may be used in the method according to the invention.

The degree of purity of the enzyme employed is not critical. The enzyme may be used in situ or after complete or partial isolation from its natural biological environment. Also, a crude extract of the organism or a tissue thereof may be used. The enzyme may also have been obtained after precipitation with e.g. ammonium sulphate. The enzyme may be present in crystalline form or be enclosed within micelles. The biochemical literature is rich in detailed information about the purification and isolation of glycosidases. The enzyme may be produced with recombinant techniques. Then, if desired, one or more of the amino acids in the amino acid sequence of the enzyme may be changed in order to optimise the properties of the enzyme, e.g. thermostability, catalytic efficiency and/or regioselectivity.

The enzyme may be used in soluble form or may be immobilised by e.g. adsorption, encapsulation, chelation, precipitation or covalent binding to a solid support, such as a polymeric substance, or a derivative thereof which is insoluble in protic or aprotic solvents (Methods in Enzymology, vol. 44, Academic Press, 1976). The form selected is not critical to the invention. If the enzyme is used in soluble form, it may first have been chemically modified in a suitable manner in order to e.g. increase the thermostability or the stability in organic cosolvents. Enzyme immobilised to an insoluble polymer comprising, for example, agarose, cellulose, hydroxyethyl acrylate, glass, silica, polyacrylic amide, polyacrylate-based plastics, etc., is readily separated from the product mixture, and the enzyme may thus be reused. An additional advantage is that in many cases a certain stabilisation against elevated temperatures and organic cosolvents is obtained.

The synthetic procedure according to the invention can be carried out under highly diverse conditions as regards, for example, pH, type of buffer, temperature and concentration of the reactants. Various cosolvents (N,N-dimethyl formamide, acetonitrile, dimethyl sulphoxide, dioxane, pyridine, methanol, ethanol, ethylene glycol, etc) may be used and in varying concentrations together with water. Moreover, the reactions can be carried out in two-phase system: water-organic solvent.

The reaction conditions are not critical but are selected primarily on the basis of the properties of the reactants employed in the synthesis concerned, and also on the basis of practicality. For example, it may be mentioned that it is usually convenient to use room temperature with enzymes and, in the case of water-rich medium, the pH is usually in the range 4–11.

Organic cosolvents may be used to minimise the hydrolytic side-reaction. For the same reason, two-phase systems may be used. Examples of cosolvents are tetrahydrofurane, acetonitrile, DMF. The choice of solvent and of the concentration or organic solvent can easily be made by the expert and does no limit the scope of the invention. Use of high concentrations of organic solvent (ca 50% and up to almost 100% of the total volume solvent) can be especially advantageous when hydrophobic acceptor derivatives which has good solubility in organic solvents are used, e.g. acceptors modified with ester groups (e.g. acetyl-, bensoyl-, butanoyl-, pivaloyl-, octanoyl-grupper, etc.) and/or with for example allyl-, benzyl-, trityl- or other groups. In this way relatively high concentration of the acceptor can be achieved in organic solvents and the hydrolytic side-reaction can be decreased due to the low water content. The method according to the invention allows synthesis in organic solvent of e.g. trisaccharide derivatives and higher oligosaccharide derivatives with exoglycosidases by using hydrophobic protected derivatives of di-, or oligosaccharides, which has only one or a few free hydroxyl groups, as acceptors.

To increase the solubility/availability and facilitate the reaction with the donor substance, one can use for example phenyl boronate, which form a complex with saccharides with vicinal diols and the resulting donor-boronate complex has, because of the phenyl group, a higher solubility in organic solvents.

The reaction temperature may also be varied to influence product yield and the stability of the enzyme and does not restrict the scope of the invention. The temperature most frequently used lies in the range 4°–55 ° C, but lower temperatures and temperatures below 0° C. can be used if organic cosolvent is used. Higher temperatures can be used with thermostable glycosidases and substrates, and also with enzymes stabilised against thermal denaturation by employing, for example, high substrate concentrations (Johansson et al, Biotechnol. Lett., 8 (1986) 421–424). An advantage with high temperatures is, for example, that high substrate concentrations may be used, which reduces the water activity and thus increases the yield of product. Another advantage is that the activity of the enzyme increases, which means shorter reaction times at increased temperatures. One additional advantage is that glycosides, e.g. methyl or ethyl glycosides, which are hydrolysed slowly at room temperature can be used as suitable glycosyl donors at increased temperatures (50°–60° C.). The upper temperature limit is determined by the thermostability of the enzyme in the reaction medium. For some transglycosidations, a lower temperature was found to give a higher yield of product glycoside.

The concentration of the acceptor is a parameter which can be used to influence the yield of the reactions according to invention. High concentrations are preferrable in both equilibrium and transglycosylation reactions to mimimize hydrolytic side-reactions, which usually means that depending on the solulility of the acceptor, ca 0.2–7M concentration of acceptor is used. A high concentration of donor is often used in equilibrium reactions. In general, high concentrations of substrates are obtained by heating the reaction mixture to near the boiling point for a few minutes, allowing the solution to cool to 37°–75° C. (depending on the thermostability of the enzyme/substrate) and then add the enzyme. Cosolvents can be used to increase the solubility of substrates with hydrophobic groups.

The reaction can be monitored by means of TLC, HPLC, or by spectrophotometric measurement of liberated aglycon (e.g. p-nitrophenol, 400 nm). When maximum yield of the product glycoside has been obtained the reaction is terminated by denaturation of the enzyme by changing the pH, increasing the temperature and/or adding organic cosolvent (such as ethanol). Heating to 80°–85° C. for 3–5 min, followed by addition of ethanol to a concentration of about 80 %, usually is sufficient.

Various techniques may be used for isolation of the product. Precipitation with e.g. an organic solvent such as ethanol is useful, especially when an excess of one of the reactants is used or when the donor, acceptor or products have different solubilities. After the equilibrium controlled synthesis or the transglycosylation reaction and after e.g. heat treatment as above and dilution of the reaction mixture, it can be useful to add a second glycosidase, which has a different regioselectivity than the glycosidase used in the synthesis. In this way, unwanted regioisomers (for example with 1-6-linkages) may be more or less selectively hydrolysed, which facilitates isolation of the desired product. Precipitation and hydrolysis of byproducts are complementary to chromatography (adsorption chromatography, gel filtration with for example, Sephadex G10-G25, HPLC with, for example, aminosilica, reversed phase silica or the new Dionex columns).

Some examples of how the invention can be used in practice, but which by no means are meant to restrict the scope of the invention, are given below.

EXAMPLE 1

Synthesis of peracetylated Gal$\alpha$1-3(2-O-allyl)Gal$\alpha$-OMe; metyl (2-O-allyl-3-O-$\alpha$-D-galactopyranosyl)-$\alpha$-D-galactopyranoside: 2-O-allyl-Gal$\alpha$-OMe (metyl 2-O-allyl-$\alpha$-D-galactopyranoside; 0.4 g) was dissolved in sodium phosphate buffer (pH 6.5, 18 ml, 0.05M) and p-nitrophenyl $\alpha$-D-galactopyranoside Gal$\alpha$-OPhNO$_2$-p; 50 mg) was added together with 400 galactosidase (Sigma; 20 U) at room temperature. More donor (Gal$\alpha$-OPhNO$_2$-p) was added and in portions (50 mg; 10 portions) during the reaction as the donor was consumed. After ca 20 h reaction the solution was heated for ca 5 minutes to inactivate the enzyme and the product was purified with column chromatography (Sephadex G10 followed by kisel gel column and after acetylation repeated column chromatography with kisel gel as solid phase). NMR of the acetylated product was used to confirm the structure.

EXAMPLE 2

Synthesis of peracetylated Gal$\alpha$1-3(2-O-benzyl)Gal$\alpha$-OMe; metyl (2O-benzyl-3-O-$\alpha$-D-galactopyranosyl)-$\alpha$-D-galactopyranoside: 2-O-benzyl-Gal$\alpha$-OMe (metyl 2-O-benzyl-$\alpha$-D-galactopyranoside; 0.4 g) was dissolved in sodium phosphate buffer (pH 6.5, 18 ml, 0.05 M) and p-nitrophenyl $\alpha$-D-galactopyranoside (Gal$\alpha$-OPhNO$_2$-p; 50 mg) was added together with 400 μl $\alpha$-D-galactosidase (Sigma; 20 U) at room temperature. More donor (Gal$\alpha$-OPhNO$_2$-p) was added and in portions (50 mg; 10 portions) during the reaction to compensate for the consumption of donor. After ca 20 h reaction the solution was heated for ca 5 minutes to inactivate the enzyme and the product was isolated with column chromatography with the same techniques as described in Example 1. NMR of the acetylated substance was used to confirm the structure.

EXAMPLE 3

Synthesis of peracetylated Gal$\alpha$1-3(2-O-allyl-6-O-allyl)Gal$\alpha$-OMe; metyl (2-O-allyl-6-O-allyl-3-O-$\alpha$-D-galactopyranosyl)-$\alpha$-D-galactopyranoside): 2-O-allyl-6-O-allyl-Gal$\alpha$-OMe (metyl-2-O-allyl-6-O-allyl-$\alpha$-D-galactopyranoside; 0.4 g) was dissolved in sodium phosphate buffer (pH 6.5, 18 ml, 0.05 M) and p-nitrophenyl $\alpha$-D-galactopyranoside (Gal$\alpha$-OPhNO$_2$-p; 50 mg) was added together with 400 μl $\alpha$-D-galactosidase (Sigma; 20 U) at room temperature. More donor (Gal$\alpha$-OPhNO$_2$-p) was added and in portions (50 mg; 10 portions) during the reaction to compensate for the consumption of donor. After ca 20 h reaction the solution was heated for ca 5 minutes to inactivate the enzyme and the product was isolated with column chromatography with the same techniques as described in Example 1. NMR of the acetylated substance was used to confirm the structure.

EXAMPLE 4

Synthesis of peracetylated Gal$\beta$1-3(2-O-benzyl)Gal$\beta$-OBn; benzyl (2-O-benzyl-3-O-$\beta$-D-galactopyranosyl)-$\beta$-D-galactopyranoside: 2-O-benzyl-Gal$\beta$OBn (metyl 2-O-benzyl-$\beta$-D-galactopyranoside; 0.4 g) was dissolved in sodium acetate buffer (pH 5.5, 18 ml, 0.05M) and o-nitrofenyl $\beta$-D-galactopyranoside (Gal$\beta$-OPhNO$_2$-o) was added at room temperature and in portions (50 mg, 10 portions) as it was consumed. The reaction and the purification was carried out principally as in the examples above, with the exception that a $\beta$-galactosidase (Aspergillus niger; Sigma; St. Louis, USA) was used as the catalyst. NMR of the acetylated substance was used to confirm the structure.

EXAMPLE 5

Synthesis of Neu5Ac$\alpha$2-3((2-O-allyl-6-O-allyl)Gal$\beta$-OMe: 2-O-allyl-6-O-allyl-Gal$\beta$-OMe (metyl-2-O-allyl-6-O-allyl-$\beta$-D-galactopyranoside; 0.4 g) was dissolved in sodium acetate buffer (pH 5.0, 18 ml, 0.05M) och p-nitrofenyl 5-acetamido-3,5 -dideoxy-alfa-D-glycero-D-galacto-2-nonulopyranosylonic acid (Neu5Ac$\alpha$-OPhNO$_2$-p) was added at room temperature and in portions (50 mg each, 10 portions) as it was consumed. The reaction and the isolation was performed as described above except that a $\alpha$-sialidase (Vibrio cholerae; Sigma) was used as catalyst and the product was purified with column chromatography without previous acetylation.

EXAMPLE 6

Synthesis av peracetylated GlcNAc$\beta$1-3(2-O-allyl-6-O-allyl)Gal$\beta$-OMe: 2-O-allyl-6-O-allyl-Gal$\beta$-OMe (metyl-2-O-allyl-6-O-allyl-$\beta$-D-galacto-pyranoside; 0.4 g) was dissolved in sodium acetate buffer (pH 6.5, 18 ml, 0.05M) and GlcNAc$\beta$-OPhNO$_2$-p (50 mg) was added at room temperature as it was consumed. The reaction and the purification of the product was performed principally as in the examples above, except that a $\beta$-D-N-acetylglucosaminidase was used as catalyst. NMR of the product was used to confirm the structure.

EXAMPLE 7

Synthesis of derivatives of Gal$\beta$1-3GlcNAc and Gal$\beta$1-4GlcNAc, respectively (constituents of Lewis-bloodgroup substances, such as Lewis-a, Lewis-x and sialylated struktures): By using for example derivatised glycoside of N-acetylglucosamine, such as e.g. structures XIII or XIV, as acceptor dissolved in for example (1/1 V/V) tetrahydrofurane:sodium acetate buffer (pH 5.5, 0.05M), Gal$\beta$-OPhNO$_2$-o as donor, and $\beta$-galactosidase as catalyst, structures of the types below can be obtained.

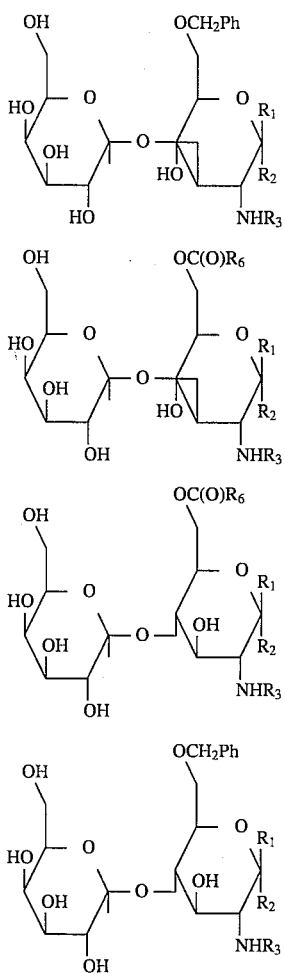

Such structures can be used directly in various applications, or can be used for further chemical or enzymatic synthesis. The galactosyl moiety can for example be modified with chemical or enzymatic methods (lipase or galactose oxidase, followed by chemical modification) leaving one free hydroxyl group in the glucosaminyl-moiety, which then can be modified with for example a fucosyl group.

Similarly, by using an acceptor of the type below, the corresponding β-bound 3-O-protected Gal-GlcNAc-derivative can be obtained.

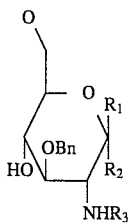

After protection of the free hydroxylgroups in the product and deprotection of the 3-O-position can, for example, an s-bound L-fucosyl group be introduced, which gives the Lewis-x structure, which can be, for example, sialylated to give e.g. NeuAcα2-3Galβ1-4(Fucα1-3)GlcNAc-R. In an analogous way, one can produce regioisomers, such as Galβ1-3(Fucα1-4)GlcNAc-R, and analogs/derivatives of Lewis-x, Lewis-a, and of sialylated Lewis-substances.

Also, with glucal modified in the 6-position as acceptor substance, with 5-galactosidase as catalyst and Galβ-OPhNO$_2$-o as donor, one obtains 5-bound galactosyl-(6-O-R)glucal.

EXAMPLE 8

Synthesis of β-galactosyl-1,2-anhydro-α-D-glucofuranoside: 1,2-anhydro-α-D-glucofuranoside was dissolved in 1/1 (V/V) tetrahydrofurane:sodium acetate buffer (pH 5.0, 0.05M) and Galβ-OPhNO$_2$-o was added at room temperature and in portions as it was consumed. The reaction was performed with β-galactosidase as catalyst and the product was isolated with column chromatography.

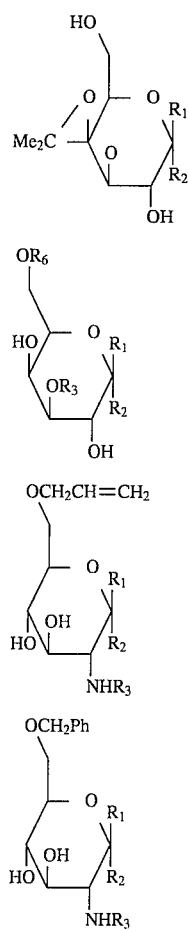
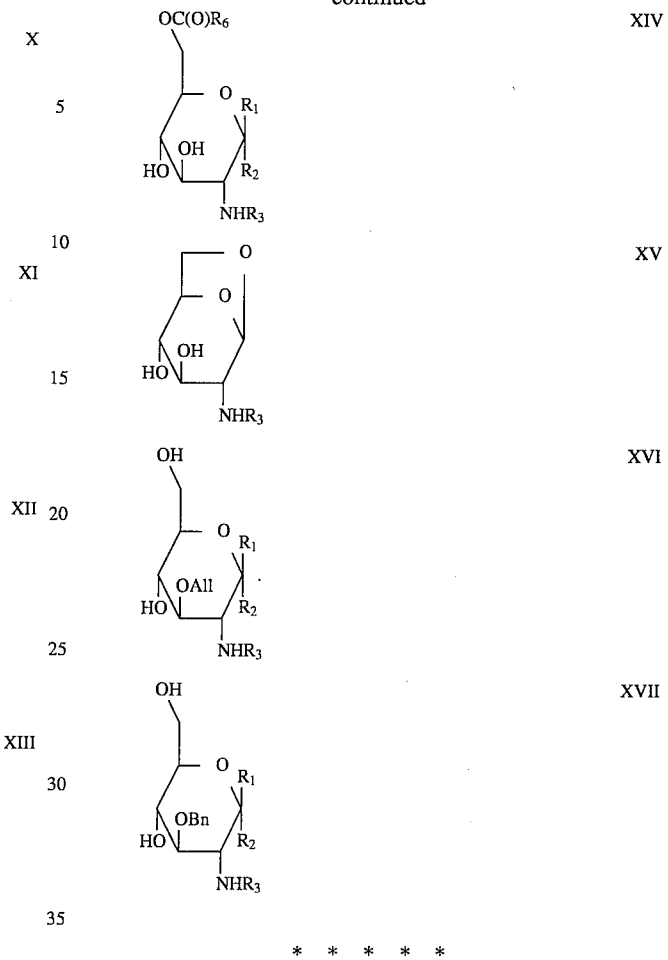

I claim the following:

1. A method for synthesizing a di-, tri- or higher oligosaccharide product, said method comprising
   (1) reacting
      (a) a glycosyl donor comprising a monosaccharide, disaccharide, oligosaccharide or glycoside,
      (b) an acceptor represented by one of the following formulae:

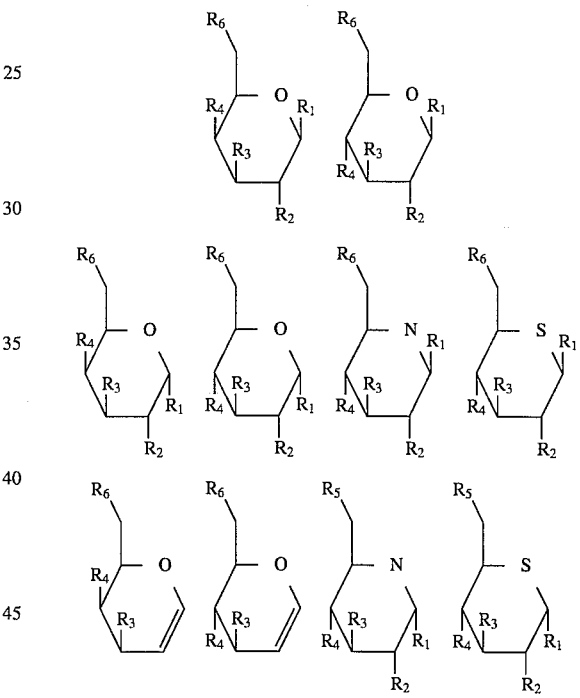

wherein $R_1$, $R_2$, $R_3$, $R_4$, or $R_6$ is —OH, —F, or an inorganic or organic group as defined below, wherein at least one and a maximum of three of $R_2$, $R_3$, $R_4$, and $R_6$ are not —OH, wherein if $R_1$ is an organic or inorganic group then said organic or inorganic group is selected from the group consisting of —OMe, —OAll, —OPh, —OCH$_2$Ph, —OEtBr, —OEtSiMe$_3$, —O(CH$_2$)$_3$CH═CH$_2$, —SMe, —SEt, and —SPh, where in if $R_2$, $R_3$, $R_4$ and/or $R_6$ is an organic or inorganic group then said organic or inorganic group is selected from the group consisting of —OMe, —OAll, —Oph, —OCH$_2$Ph, —OEtBr, —OEtSiMe$_3$, —O(CH$_2$)$_3$CH═CH$_2$, —SMe, —SEt, —SPh, —NHAc, N-chloromethoxyacetyl-, N-phenoxyacetyl-, —NHBOC, —NHOH, —N$_3$, p-methoxybenzyl ether, trityl, trialkylsilyl ether, pivaloyl, tetrahydropyranyl, (2-methoxyethoxy)methylisopropylidene ketal, cyclohexylidene ketal, benzylidene acetal, orthoester, —ONO₃, tosylate, mesylate, sulfate, phosphate, and carboxylate, with the proviso that R₂ is not —NHAC, and (c) an E.C. group 3.2 endo- or exoglycosidase to form said product, wherein said glycosyl donor transfers a carbohydrate group to said acceptor to form said product, and (2) optionally isolating said product.

2. The method as claimed in claim 1, wherein said acceptor is in the furanose form or in the pyranose form.

3. The method as claimed in claim 1, wherein R₂ is —NHOH, —NHBOC, —N₃, —N-phenoxyacetyl- or —N-chloromethoxyacetyl.

4. The method as claimed in claim 1, wherein said organic group is acetyl-, benzoyl-, pivaloyl-, allyl-, benzyl-, p-methoxybenzyl, p-isopropylidene-, or benzylidene.

5. The method as claimed in claim 1, wherein said inorganic group is carboxylate-, sulphate-, phosphate-, —NHOH— or —N₃.

6. The method as claimed in claim 1, wherein said acceptor consists of galactal, glucal or consists of galactal or glucal wherein at least one and a maximum of two of R₃, R₄, and R₆ are not —OH.

7. The method as claimed in claim 1, wherein said glycosyl donor contains one or more of the monosaccharide residues D-galactose, D-mannose, N-acetylneuraminic acid, N-acetyl-D-galactosamine, N-acetyl-D-glucosamine or L-fucose, containing a glycosidically bound organic group.

8. The method as claimed in claim 1, wherein said glycosidase is a galactosidase, fucosidase, hexosaminidase, N-acetylglucosaminidase, or a N-acetyl-galactosaminidase.

9. The method as claimed in claim 1, wherein said glycosidase is an in situ or isolated naturally occurring or recombinant glycosidase.

10. The method as claimed in claim 1, wherein said glycosidase is immobilized via precipitation, adsorption, enclosure, chelation, or covalent binding, to a polymeric substance which is insoluble in protic or aprotic solvents.

11. The method as claimed in claim 10, wherein said polymeric substance is selected from the group consisting of a polysaccharide, a plastic, a copolymer, silicate, and a glass.

12. A di-, tri- or oligosaccharide product synthesized by the method according to claim 1.

13. The method as claimed in claim 1, further comprising protecting the hydroxyl groups of said product and deprotecting said product to give one free hydroxyl group in one of positions C-2, C-3, C-4, C-5 or C-6, in a chemical synthesis for obtaining a disaccharide derivative, a trisaccharide or a higher oligosaccharide, or a derivative thereof.

14. The method as claimed in claim 1, wherein said glycosidase is α-N-acetyl-galactosaminidase, wherein said glycosyl donor is N-acetyl-galactosamine or a glycoside thereof, and wherein said acceptor is galactose, or a derivative or glycoside thereof, modified in the hydroxyl group of position C-2, or of C-2 and in one of the positions C-4 or C-6, said method further comprising protecting the hydroxyl groups of said product DOA and then deprotecting said product to give a hydroxyl group in the C-2 position, in a chemical synthesis of blood group determinant A or a derivative thereof.

15. The method as claimed in claim 1, wherein said glycosidase is α-galactosidase, wherein said glycosyl donor is galactose or a glycoside thereof, and wherein said acceptor is galactose, or a derivative or glycoside thereof, modified in the hydroxyl group of position C-2, or of C-2 and in one of the positions C-4 or C-6, said method further comprising protecting the hydroxyl groups of said product DOA and deprotecting said product to give a hydroxyl group in the C-2 position, in a chemical synthesis of blood group determinant B or a derivative thereof.

16. The method as claimed in claim 1, wherein said glycosidase is β-galactosidase, wherein said glycosyl donor is galactose, lactose or a β-galactoside, and wherein said acceptor is a 3-O-protected N-acetyl-glucosamine or a 3-O-protected derivative thereof, said method further comprising protecting the hydroxyl groups of said 3-O-protected product DOA and deprotecting said product to give a hydroxyl group in the C-3 position, in a chemical synthesis of Lewis-x or a derivative thereof.

17. The method as claimed in claim 1, wherein said glycosidase is α-fucosidase, wherein said glycosyl donor is an α-fucoside, and wherein said acceptor is a 3-O-protected N-acetyl-glucosamine or a 3-O-protected derivative thereof said method further comprising protecting the hydroxyl groups of said 3-O-protected product DOA and deprotecting said product to give a hydroxyl group in the C-3 position, in a chemical synthesis of Lewis a or a derivative thereof.

18. The method as claimed in claim 1, wherein said glycosidase is α-sialidase, wherein said glycosyl donor is N-acetylneuraminic acid or a glycoside thereof, and wherein said acceptor is galactose, or a derivative or glycoside thereof, modified in at least one and maximum three of the hydroxyl groups of C-2, C-4, or C-6, and that the product is used in the chemical synthesis of sialylated Lewis-a, sialylated Lewis-x or a derivative thereof or of sialylated di-, tri- or oligosaccharides or derivatives thereof.

19. The method as claimed in claim 1, wherein the product DOA obtained in the glycosidase-catalysed process, is used in an enzymatic synthesis for obtaining a disaccharide derivative, a trisaccharide or a higher oligosaccharide, or a derivative thereof.

20. The method as claimed in claim 13, wherein said glycosidase is α-N-acetyl-galactosaminidase, wherein said glycosyl donor is N-acetylgalactosamine or a glycoside thereof, and wherein said acceptor is galactose, or a derivative or glycoside thereof, modified in the hydroxyl group of position C-2, or of C-2 and in one of the positions C-4 or C-6, said method further comprising protecting the hydroxyl groups of said product DOA, and then deprotecting said product to give a hydroxyl group in the C-2 position, in a chemical synthesis of blood group determinant A or a derivative thereof.

21. The method as claimed in claim 13, wherein said glycosidase is α-galactosidase, wherein said glycosyl donor is galactose or a glycoside thereof, and wherein said acceptor is galactose, or a derivative or glycoside thereof, modified in the hydroxyl group of position C-2, or of C-2 and in one of positions C-4 or C-6, said method further comprising protecting the hydroxyl groups of said product DOA and deprotecting said product to give a hydroxyl group in the C-2 position, in a chemical synthesis of blood group determinant B or a derivative thereof.

22. The method as claimed in claim 13, wherein said glycosidase is β-galactosidase, wherein said glycosyl donor is galactose, lactose or a β-galactoside, and wherein said acceptor is a 3-O-protected N-acetyl-glucosamine or a 3-O-protected derivative thereof, said method further comprising protecting the hydroxyl groups of said 3-O-protected product DOA and deprotecting said product to give a hydroxyl group in the C-3 position, in a chemical synthesis of Lewis-x or a derivative thereof.

23. The method as claimed in claim 13, wherein said glycosidase is α-fucosidase, wherein said glycosyl donor is an α-fucoside, and wherein said acceptor is a 3-O-protected N-acetyl-glucosamine or a 3-O-protected derivative thereof said method further comprising protecting the hydroxyl groups of said 3-O-protected product DOA and deprotecting said product to give a hydroxyl group in the C-3 position, in a chemical synthesis of Lewis a or a derivative thereof.

24. The method as claimed in claim 11, wherein said polysaccharide is cellulose or agarose and said plastic is polyacrylamide, polyvinylalcohol, or polystyrene.

25. The method as claimed in claim 1, wherein said glycosyl donor is Galα-OPhNO₂-p, wherein said acceptor is 2-O-allyl-Galα-OMe, wherein said glycosidase is α-D-galactosidase, and wherein said product is Galα1-3(2-O-allyl)Galα-OMe.

26. The method as claimed in claim 1, wherein said glycosyl donor is Galα-OPhNO₂-p, wherein said acceptor is 2-O-benzyl-Galα-OMe, wherein said glycosidase is α-D-galactosidase, and wherein said product is Galα1-3(2-O-benzyl)Galα-OMe.

27. The method as claimed in claim 1, wherein said glycosyl donor is Galα-OPhNO₂-p, wherein said acceptor is 2-O-allyl-6-O-allyl-Galα-OMe, wherein said glycosidase is α-D-galactosidase, and wherein said product is Galα1-3(2-O-allyl-6-O-allyl)Galα-OMe.

28. The method as claimed in claim 1, wherein said glycosyl donor is Galβ-OPhNO₂-o, wherein said acceptor is 2-O-benzyl-Galα-OBn, wherein said glycosidase is β-galactosidase, and wherein said product is Galα1-3(2-O-benzyl)Galα-OBn.

29. The method as claimed in claim 1, wherein said glycosyl donor is Neu5Acα-OPhNO₂-p, wherein said acceptor is 2-O-allyl-6-O-allyl-Galβ-OMe, wherein said glycosidase is α-sialidase, and wherein said product is Neu5Acα2-3 (2-O-allyl-6-O-allyl)Galα-OMe.

30. The method as claimed in claim 1, wherein said glycosyl donor is GlcNAcβ-OPhNO₂-p, wherein said acceptor is 2-O-allyl-6-O-allyl-Galα-OMe, wherein said glycosidase is β-D-N-acetylglucosiaminidase, and wherein said product is GlcNAcβ1-3(2-O-allyl-6-O-allyl)Galβ-OMe.

31. The method as claimed in claim 1, wherein said glycosyl donor is Galβ-OPhNO₂-o, wherein said acceptor is 1,2-anhydro-α-D-glucofuranoside, wherein said glycosidase is β-galactosidase, and wherein said product is β-galactosyl-1,2-anhydro-α-D-glucofuranoside.

32. The method as claimed in claim 1, wherein said acceptor is D-galactal, D-glucal or D-galactal or D-glucal wherein at least one of $R_3$, $R_4$, and $R_6$ are not —OH.

33. The method as claimed in claim 1, wherein said acceptor is D-galactopyranose or D-glucopyranose wherein at least one of $R_2$, $R_3$, $R_4$, and $R_6$ are not —OH.

34. The method as claimed in claim 1, wherein said acceptor is one of the following formulae:

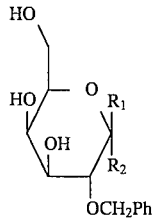   I

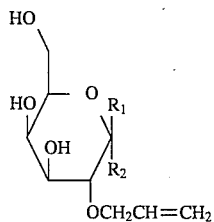   II

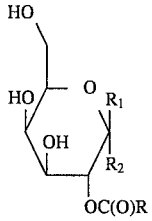   III

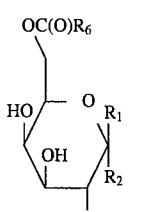   IV

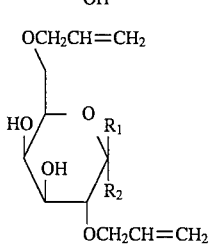   V

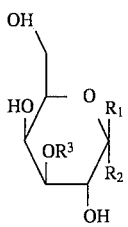   VI

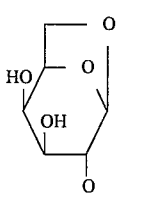   VII

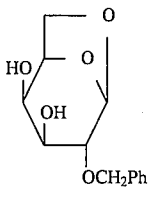   VIII

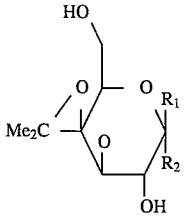   IX